United States Patent [19]

Finucane et al.

[11] Patent Number: 5,661,120
[45] Date of Patent: Aug. 26, 1997

[54] SOAP BAR COMPOSITION COMPRISING LOW LEVELS OF SILICONE AS PROCESSING AIDS

[75] Inventors: Kevin Michael Finucane, Saddle Brook; Frederick Silvio Osmer, Parsippany, both of N.J.; James Joseph Corr, Dix Hills, N.Y.

[73] Assignee: Lever Brothers Company, Division of Conopco, Inc., New York, N.Y.

[21] Appl. No.: 266,992

[22] Filed: Jun. 27, 1994

Related U.S. Application Data

[63] Continuation of Ser. No. 5,715, Jan. 19, 1993, abandoned.

[51] Int. Cl.⁶ .......................................................... C11D 9/36
[52] U.S. Cl. .......................... 510/153; 510/141; 510/152; 510/155; 510/156; 510/466
[58] Field of Search .............................. 282/549, DIG. 16, 282/174.15; 510/141, 152, 153, 155, 156, 466, 445, 447, 450

[56] References Cited

U.S. PATENT DOCUMENTS

| | | | |
|---|---|---|---|
| 4,673,525 | 6/1987 | Small et al. | 252/135 |
| 4,919,838 | 4/1990 | Tibbetts et al. | 252/134 |
| 4,976,953 | 12/1990 | Orr et al. | 424/70 |
| 5,011,681 | 4/1991 | Ciotti et al. | 424/81 |
| 5,085,857 | 2/1992 | Reid et al. | 424/20 |
| 5,152,914 | 10/1992 | Forster et al. | 252/174 |
| 5,154,849 | 10/1992 | Visscher et al. | 252/134 |
| 5,308,526 | 5/1994 | Dias et al. | 252/125 |
| 5,433,894 | 7/1995 | Massaro et al. | 252/549 |
| 5,439,682 | 8/1995 | Wivell et al. | 424/401 |

*Primary Examiner*—Paul Lieberman
*Assistant Examiner*—Necholus Ogden
*Attorney, Agent, or Firm*—Ronald A. Koatz

[57] ABSTRACT

The invention describes detergent bar compositions comprising liquid silicone compounds or emulsions of said compounds which are used in relatively small levels as processing aids. These compounds allow pellets coming off a chill roll or refiner to be less tacky such that they do not readily clog machinery when the pellets are transferred to silos.

7 Claims, 1 Drawing Sheet

SOAP BAR COMPOSITION COMPRISING LOW LEVELS OF SILICONE AS PROCESSING AIDS

This is a continuation application of Ser. No. 08/005,715 filed Jan. 19, 1993, now abandoned.

BACKGROUND OF THE INVENTION

1. Field of the Invention

The present invention relates to soap bar composition in which most or all of the soap has been replaced by other surfactants. Typically, when enough soap has been removed, the compositions are softer, stickier and accordingly more difficult to process. The present invention relates in particular to the use of small amounts of silicone or mixtures of silicones of defined viscosity (i.e., centistokes) which allow the detergent bars to be more efficiently processed.

2. Background

Traditionally, soap has been utilized as a skin cleaner. Soap is, however, a very harsh chemical. Irritated and cracked skin result from the use of soap, especially in colder climates. There are, however, certain benefits from the use of soap including less cost, ease of manufacture into bars, and good lathering properties.

Thus, there is a balance between attempting to replace soap with milder surfactants, on the one hand, and attempting to maintain manufacturing ease associated with use of soap on the other hand.

For example, if the amount and type of milder replacement surfactants which are added is too great, the soap pellets (i.e., chips) formed during manufacture (i.e., formed after mixing the ingredients, solidifying on a chill roll, and refining to form chips) will be too "soft". That is to say, the pellets or chips/noodles will melt on a valve used to transfer the chips to storage in a container/silo. Clogging the machinery such that the chips cannot be readily stored means that the process cannot be stopped and chips cannot be stored until a future time when the chips will be further mixed, refined, extruded, cut and stamped. That is, failure to allow storage means that the first part of the process cannot be run as a batch process (where chips can be stored) and must be run from mixing of ingredients until bar extrusion and stamping. This present invention is directed to those compositions which can be readily processed from chip formation to silo storage thereby allowing an intermediate storage step.

Typically such compositions are those in which the amount of soap used is at very low levels relative to surfactant, i.e., at level under 25% by weight of the composition, usually under 15% by weight.

Another way of looking at the problem is to determine when the composition of the pellets is sufficiently tacky that they clog machinery and lower throughput levels (i.e., rate of plodded bars coming out of a plodder) to economically unacceptable rates.

In applicants, co-pending application filed on the same day as the subject application and entitled "Low Soap Bar Composition Having Optimal Throughput at Lower Temperatures", applicants claim compositions wherein the throughput rate of a bar made from processing said composition through a plodder is higher at a temperature below 100° F. than it is above 100° F. This is unexpected in that normally it would not be possible to simultaneously process a bar at such high rates and at such low temperatures because the bar would be too hard, while at higher temperatures the bar would be too soft and not process at all.

While the compositions of the co-pending application are similar to those of the subject invention, there is no teaching in that application of adding specific silicone (i.e., of specific viscosity) in specific amounts in order to eliminate the problem of tacky pellets coming from the chill roll and refiner (e.g., so that they don't stick on the valve in the rotator) while passing the pellets/chips to a silo.

The use of silicone in bar compositions comprising silicone is known in the art, for example, from U.S. Pat. No. 5,154,849 to Visscher et al. (assigned to Procter & Gamble).

In the prior art compositions, silicone is used as a skin mildness/moisturizing aid and must be used in amounts sufficient to perceive these effects (e.g. from about 0.5% to about 20%). Thus, the silicone appears always to be used in amounts of at least several percents by weight (In the patent it is never exemplified at less that 5% as in Examples XII & XIII). There is certainly no recognition of a critical window not only in amount (i.e., from about 0.1 to about 0.9% by weight), but also in the viscosity of the silicone as in the silicone of the present invention. The Visscher patent also requires the presence of at least some silicone gum (claim 1) and this gum must have a molecular weight of at least 200,000 (claim 9). The silicone of the subject invention is used in the absence of gum and is not itself a silicone gum.

BRIEF SUMMARY OF THE INVENTION

Surprisingly and unexpectedly, applicants have found that the tackiness values (associated with use of milder than soap actives) responsible for clogging machinery needed to transfer soap chips/noodles from the refiner to the silo can be lowered by utilizing defined silicone in defined amounts in the compositions. While not wishing to be bound by theory, it is believed that the defined window of silicone lubricates these compositions just enough so that they process more readily without clogging or sticking to machinery. As a corollary, the compositions allow a synthetic soap composition to be noodled by a refiner at a faster rate than the analogous compositions without silicone.

Specifically, the invention relates to compositions comprising (all percentages by weight):

(1) from about 10%–70% of a first synthetic surfactant which is an anionic surfactant;

(2) from about 1%–20% of a second synthetic surfactant selected from the group consisting of a second anionic surfactant (differing from the first), a nonionic surfactant, an amphoteric surfactant and mixtures thereof;

(3) 0–35% free fatty acid;

(4) 0–25% soap; and (5) 0.1–0.9% preferably 0.1–0.75, more preferably 0.1–0.50% of a silicone compound or mixtures of silicone compounds having a viscosity of from about 10,000 centistokes preferably 10,000–200,000, more preferably 10,000–150,000, most preferably 10,000–100,000. Alternatively the silicone compound may be defined as having a molecular weight of from about 60,000 to 200,000, preferably 60,000 to 175,000, most preferably 60,000 to 140,000.

In a second embodiment of the invention the invention provides a method of reducing stickiness and increasing noodle rates of soap noodles passing from a refiner to a silo for storing said noodles prior to subsequent processing which method comprises mixing 10–70% of a first synthetic surfactant which is an anionic surfactant; from 1%–20% of a surfactant selected from the group of surfactants consisting of second anionic (differing from the first), a nonionic surfactant, an amphoteric surfactant and mixtures thereof; 0-25% free fatty acid, 0-35% soap and 0.1-0.9% of a silicone compound as defined above.

DETAILED DESCRIPTION OF THE INVENTION

Figure 1:
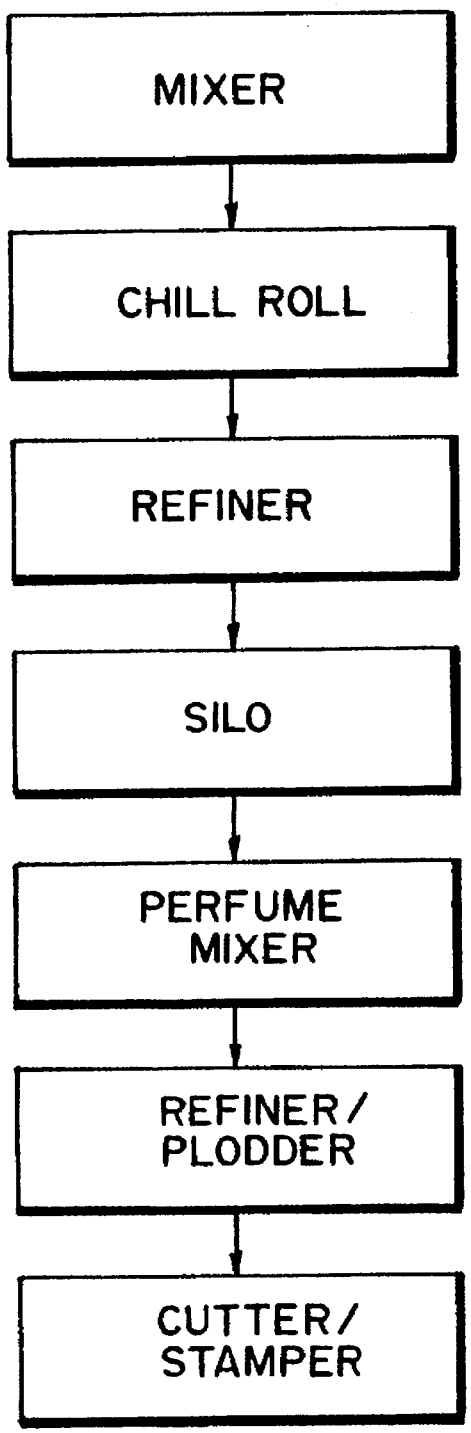
FIG. 1 is a schematic drawing of 7 steps normally taken in preparation of final bar from mixing to cutting. In the absence of silicone component of invention, throughput rates at steps 3 and 4 become so low that overall production rates are severely reduced.

In one embodiment of the invention, the invention relates to a synthetic soap bar composition comprising 0.01-0.9% by weight of a silicone component or a mixture of specified silicone components (1) providing improved noodle or chip rate production (e.g., serving as a processing aide) after the composition is mixed, chill rolled and refined and (2) lowering tackiness of the noodles (as measured from bar composition minus final additives such as perfume and colorants).

Specifically this embodiment of the invention includes a synthetic soap bar composition comprising:

(1) from about 10% to about 70% of a first synthetic surfactant which is an anionic surfactant;

(2) from about 1% to 20% of a second surfactant selected from the group consisting of a second anionic surfactant (differing from the first), a nonionic surfactant, an amphoteric surfactant and mixtures thereof;

(3) 0-35% from fatty acid;

(4) 0-25% soap; and (5) 0.1 to 0.9%, preferably 0.1 to 0.75, more preferably 0.1 to 0.5% of a single silicone compound or mixture of silicone compounds having a viscosity over 10,000 centistokes, preferably 10,000 to 200,000; more preferably 10,000-150,000, most preferably 10,000-100,000.

Use of this silicone compound or mixture of silicone compounds allows soap chips/noodles formed from the mixing of these compounds to be made in a batch process and stored in a container or silo, if desired, prior to further refining, plodding and stamping. Thus this allows the process to be decoupled such that noodles can be stored and later used rather than having to utilize the noodles as they are made.

Compositions

Typical mild detergent bar compositions will comprise less than 15% by weight soap, usually less than 5% soap and most preferably less than 3% soap.

The term "soap" is used herein in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic aliphatic (alkanoic or alkanoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12-18 carbons atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil, in which case the fatty acid content is about 85% of $C_{12}$-$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or staric ($C_{18}$) acids with an alkali metal hydroxide or carbonate.

The first anionic detergent active which may be used may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glycerol ether sulfonate (AGS); or aromatic sulfonates such as alkyl benzene sulfonate.

The first anionic may also be an alkyl sulfate (e.g., $C_{12}$-$C_{18}$ alkyl sulfate) or alkyl ether sulfate (including alkyl glycerol ether sulfates). Among the alkyl ether sulfates are those having the formula:

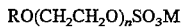

$RO(CH_2CH_2O)_n SO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono-and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates.

Sulfosuccinates may be monoalkyl sulfosuccinates having the formula $$R^4O_2CCH_2CH(SO_3M)CO_2M;$$

and amide-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula $R'CON(CH_3)CH_2CO_2M$, wherein R ranges from $C_8$–$C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to have from 6 to 10 carbon atoms.

Acyl isethionates, when present, will generally range from about 10% to about 70% by weight of the total composition. Preferably, this component is present from about 30% to about 60%.

The acyl isethionate may be an alkoxylated isethionate such as is described in Ilardi et al., U.S. Ser. No. 796,748, hereby incorporated by reference. This compound has the general formula

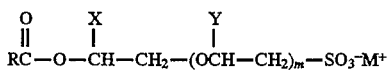

wherein R is an alkyl group having 8 to 18 carbons, m is an integer from 1 to 4, X and Y are hydrogen or an alkyl group having 1 to 4 carbons and $M^+$ is a monovelent cation such as, for example, sodium, potassium or ammonium.

In general the anionic component will comprise from about 10 to 70% of the composition, preferably 30–70%, most preferably. 40–60% of the composition.

The second component of the invention may be any of the anionic surfactants discussed above except that it should be different than the first antonic component. The second component may also be any of the amphoteric or nonionics discussed below as well as a mixture of the anionic, amphoteric and/or nonionic.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula.

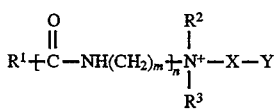

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4;

n is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

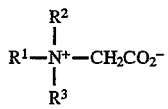

and amido betaines of formula:

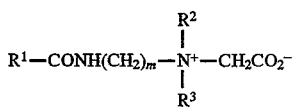

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferablly at least three quarters of the groups $R^1$ have 10 to 14 carbon atoms. $R^2$ and $R^3$ are preferably methyl.

A further possibility is that the amphoteric detergent is a sulphobetaine of formula

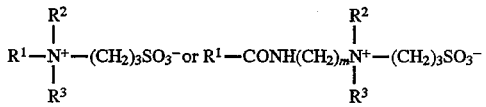

where m is 2 or 3, or variants of these in which —$(CH_2)_3SO_3$— is replaced by

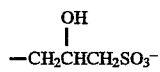

In these formulae $R^1$, $R^2$ and $R^3$ are as discussed previously.

The nonionic which may be used as the second component of the invention include in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Ser. No. 816,419 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. which is also incorporated into the subject application by reference.

In general the second component (i.e., second anionic nonionic and/or amphoteric compound or mixture) is incorporated into the composition as less than 20% by weight, preferably 1 to 15% by weight of the composition.

Free fatty acids of 8–22 carbon atoms may also be desirably incorporated within the compositions of the present invention. Some of these fatty acids are present to operate as superfatting agents and others as skin feel and creaminess enhancers. Superfatting agents enhance lathering properties and may be selected from fatty acids of carbon atoms numbering 8–18, preferably 10–16, in an amount up to 35% by weight of the composition. Skin feel and creaminess enhancers, the most important of which is stearic acid, are also desirably present in these compositions.

Skin mildness improvers also preferably used in the composition of the invention are salts of isethionate. Effective salts cations may be selected from the group consisting of alkali metal, alkaline earth metal, ammonium, alkyl ammonium and mono-, di- or tri-alkanolammonium ions. Specifically preferred cations include sodium, potassium, lithium, calcium, magnesium, ammonium, triethylammonium, monoethanolammonium, diethanolammonium or triethanolammonium ions.

Particularly preferred as a mildness improver is simple, unsubstituted sodium isethionate of the general formula wherein R is hydrogen.

The skin mildness improver will be present from about 0.5% to about 50%. Preferably, the mildness improver is present from about 1% to about 25%, more preferably from about 2% to about 15%, optimally from 3% to 10%, by weight of the total composition.

Other performance chemicals and adjuncts may be needed with these compositions. The amount of these chemicals and adjuncts may range from about 1% to about 40% by weight of the total composition. For instance, from 2 to 10% of a suds-boosting detergent salt may be incorporated. Illustrative of this type additive are salts selected from the group consisting of alkali metal and organic amine higher aliphatic fatty alcohol sulfates, alkyl aryl sulfonates, and the higher aliphatic fatty acid taurinates.

Adjunct materials including germicides, perfumes, colorants, pigments such as titanium dioxide and water may also be present.

Silicone Component

The silicone materials useful in the present invention are generally non-volatile and may be either a polyalkyl siloxane, a polyaryl siloxane, a polyalkylaryl siloxane, a polysiloxane with amino functional substitutions, or a polyether siloxane copolymer. The siloxanes useful in the present invention may be endcapped with any number of moieties, including, for example, methyl, hydroxyl, ethylene oxide, propylene oxide, amino, and carboxyl. Mixtures of these materials may also be used and are preferred in certain executions. Additionally, volatile silicones may be used as part of the silicone mixture so long as the final mixture is non-volatile.

The polyalkyl siloxanes that may be used herein include, for example, polydimethyl siloxanes with viscosities ranging from about 10,000 to about 200,000 centistokes. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970. Preferably the viscosity ranges from about 10,000 centistokes to about 150,000 centistokes and most preferably from about 10,000 centistokes to about 100,000 centistokes.

The polyalkylaryl siloxanes that may be used include, for example, polymethylphenylsiloxanes having viscosities of from about 10,000 to about 200,000 centistokes. These siloxanes are available, for example, from the General Electric Company as SF 1075 methyl phenyl fluid or from Dow Corning as 556 Cosmetic Grade Fluid. Additionally, poly(dimethyl siloxane) (diphenyl siloxane) copolymers having a viscosity in the range of from about 10,000 to about 200,000 centistokes are useful. The polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

References disclosing suitable silicones include U.S. Pat. No. 2,826,551, issued Mar. 11, 1958, Geen; U.S. Pat. No. 3,964,837, issued Dec. 21, 1982, Pader; and British Patent 849,433, Woolston, published Sep. 28, 1960. All of these patents are incorporated herein by reference. Also incorporated herein by reference is Silicon Compounds, distributed by Petrarch Systems, Inc., 1984. This reference provides a very good listing of suitable silicone material.

Silicone gums are described by Petrarch and others including U.S. Pat. No. 4,152,416, May 1, 1979, Spitzer et al., and Noll, Walter, Chemistry and Technology of Silicones, New York: Academic Press, 1968. Also describing useful silicone gums are General Electric Silicone Rubber Product Data Sheets SE30, SE 33, SE 54 and SE 76. All of these described references are incorporated herein by reference.

In a preferred embodiment of the invention, only silicone liquids or mixtures of silicone liquids having a viscosity of from about 10,000 to about 200,000, preferably 40,000 to 150,000 should be used.

The silicone component or components of the invention may be used as is or it may be used in the form of an emulsion composition, for example 50% water and 50% silicone compound. In a preferred embodiment of the invention, the silicone used in this emulsion has a viscosity of from about 10,000 to 200,000, preferably 10,000 to 150,000.

As indicated above, the component may be used as 0.1–9% by weight of the composition, preferably 0.1–0.75%, more preferably 0.1–0.0.5 of the composition.

In a second embodiment of the invention, the invention provides a process for reducing tackiness of the noodles used in the final bar composition for final additives, and of increasing the noodle rate of soap noodles passing from a refiner to a silo for storing said noodles prior to further processing wherein said process comprises mixing the various compounds of the composition at a temperature from about 150° F.–300° F. for about 15 minutes to about 24 hours depending on desired moisture values.

Processing

Typically the components of the bar formulations are intimately mixed by mixing the various components in an aqueous slurry, typically using about 6 to 15% by weight water (94 to 85% by weight solids) at a temperature of from about 100° C. to about 200° C.

The slurry can be drum-dried to a moisture content up to 9% in the dry mix. Alternatively, the components can be mixed dry, preferably in a mechanical mixer such as a Werner-Pfleiderer or Day mixer. At 85° C. (185° F.), a few hours of mixing may be necessary to dry the mixture to the desired moisture, while at 115° C. (240° F.), a smooth blend will be obtained in approximately one half hour. The time can be reduced by further increasing the temperature, which will of course be kept below a temperature at which any of the components would be degraded. All of the components can be added together, or it may be desirable to mix the lathering detergent with an amount of water first and then incorporate the other ingredients.

After the components have been mixed the composition is cooled and solidified, typically using a chilled flaker (i.e., chill roll) to form small chips. This is often followed by further cooling the chips on a so-called aging apron which is essentially a conveyer belt which carries the chips as they come out of the chill roll.

It is at this point of the process where one of the principal advantages of the invention occurs. Typically, as the chips leave the aging apron they may either (1) be placed through a refiner wherein mechanical energy is used (e.g., in the form of an airveying valve) to noodle the synthetic soap and then discharge the noodles through airveying valve into a receptacle/silo or (2) they may be further mixed, sent to a refiner/plodder, cut and stamped.

If the chips follow the first route above, they must be sufficiently hard that they don't melt and clog the machinery (e.g., cause the airveying valve to stop rotating), yet not so hard that they will not later be able to be plodded and stamped. In the absence of the silicone component(s) of the invention, throughput rates of the noodles coming through the refiner are relatively low. While not wishing to be bound by theory, this may be a combination of the fact that the chips/noodles are too soft and clog machinery over time and/or because the silicone is a process aide which mechanically helps in noodle formation. While the noodle rates are not absent altogether, the rates are low enough as to make the process economically unviable.

By contrast, when the silicone component or components of the invention are used, tackiness values are reduced and noodle rates are increased.

As a result, the use of the silicone component(s) allows a refiner and storage step to be used (i.e., be economically viable) after chips come off an aging apron (following the chill roll).

It should be noted that, since it is difficult to measure tackiness values of noodles coming out of a refiner, all tackiness values for purpose of the invention were measured on the final bar product minus final additives such as perfume and colorants.

The following examples are meant to be illustrative only and are not intended to limit the invention in any way.

EXAMPLES

Measuring

Plodder/Extruder

The extrusion of the final synthetic soap bar was not done at a commercial plant, but at a small pilot plant. All product was accordingly extruded using a Mazzoni M-150 refiner/plodder. The screw diameter was 150 mm while the pressure plate opening was 49.5 mm by 27.5 mm. The refiner screw was run at 15.0 RPM. A typical commercial packing line plodder would be a Mazzoni B300/3500 which is capable of plodding a pure soap bar composition at a rate of 3500 Kg/hr. (i.e., about 7500–8000 lbs/hr.).

Tackiness

The tackiness of the bars of the invention is measured using a tackiness measurement device as described in greater detail below:

Measurement is accomplished essentially by placing an object of known surface area and impaling this object (using the conical area of the object) into the bar billet.

Specifically, the object is a pointed metal cylinder made of aluminum which penetrates the bar. The object is shaped like a sharpened pencil or a top and comprises both a top cylindrical section and a bottom conical section which conical section initially impales the bar.

In the examples of this invention, the overall length of the pointed cylinder was 64 mm with the length of the cylindrical section being 51 mm and the length of the conical section being 13 mm. Diameter was 25.5 mm. Surface area of the cone was 729.4 mm2 or 7.294 $cm^2$. Since the entire conical section is used to impale the soap billet each time, the surface area is kept constant and the force measurements can be compared directly.

The cylinder is placed through a centering bushing located on a bridge and is positioned over the soap billet which is held in a vise attachment. The pointed cylinder is then pushed into the soap billet in such a manner that the top of the cylinder is flush with the top of the centering bushing. This ensures that the cylinder is impaled the same distance each time and therefore the surface area is constant. There is a threaded hook inserted into the top of the cylinder. This hook is positioned over an inverted hook protruding from a dynamometer (force measuring device). The dynamometer is attached to a movable arm that is driven by a low RPM motor. Once the cylinder is impaled and the hooks are correctly positioned, the motor is started and the arm begins to move upward away from the soap billet. The moving arm pulls the dynamometer which in turn pulls the cylinder. The dynamometer measures the maximum force applied exactly at the time the cylinder breaks apart from the soap billet. The test is performed three times at each temperature using three different pointed cylinders. The tackiness data is then plotted versus temperature for each bar formulation.

It should be noted that both product temperature and product water levels are kept as constant as experimentally possible The compositions tested in the following examples typically were formulated as follows:

Experimental Formula A

| Component | % by Weight |
| --- | --- |
| Fatty Acid Isethionate | about 50.00 |
| Free Fatty Acid | about 25.00 |
| Free Isethionate | about 5.5 |
| Sulfosuccinate* | about 6.0 |
| Betaine** | about 2.0 |
| Preservatives, dyes, water & other minors*** | Remainder |

*Cocoamidosulfosuccinate
**Cocoamidopropylbetaine
***For purposes of the experimental formulation, no perfume was added.

Compositions as formulated above were mixed (with and without silicone component(s) of the invention) and chilled (i.e., on a chill roll) and then further refined. For purposes of the experiment, the noodles were then placed directly in a refiner/plodder (e.g., for extrusion) cut and then stamped. The results of these experiments are set forth in the table below:

Plodding and Noodling Rates of Non-Perfumed Compositions

| Example | Silicone* Component | Average Noodle Rate lbs/hr | Temp (°F.) | % H₂O | Plodding Temp (°F.) | Penetration (mm) | Tackiness (Kg) |
|---|---|---|---|---|---|---|---|
| Comparative A | None | 393.0 | 91.8 | 4.66 | 100.2 | 7.65 | 3.47 |
| Comparative B | None | 364.0 | 94.3 | 4.00 | 100.7 | 7.49 | 2.09 |
| 1 | .5% of 60 M silicone | 528.6 | 91.6 | 4.28 | 100.0 | 8.05 | 2.73 |
| 2 | 0.1% of 50-50 emulsion of water & 60 M silicone | 588.0 | 94.0 | 3.60 | 104.67 | 6.5 | <1.0 |
| 3 | .25% of 50-50 emulsion of water and 60 M silicone | 509.1 | 90.4 | 4.54 | 100.3 | 7.90 | 3.03 |
| 4 | .5% of 50-50 emulsion of water and 60 M silicone | 612.0 | 91.5 | 4.95 | 100.0 | 7.70 | 2.58 |
| 5 | 1.0% of 50-50 emulsion of 60 M silicone | 564.9 | 87.0 | 4.65 | 100.0 | 6.81 | 3.50 |
| 6 | 1.5% of 10 M silicone** | 169.2 | 92.1 | 3.84 | 101.5 | 7.0 | <1.0 |
| 7 | 0.1% of 10 M silicone | 449.2 | 94.7 | 4.70 | 102.0 | 9.88 | <1.0 |
| 8 | 0.1% of 100 M silicone | 768.0 | 98.0 | 3.80 | 103.7 | 7.12 | 1.84 |

*In all examples, silicone component was dimethylsiloxane
**1.5% is outside defined range As can be seen from the Table above, when no silicone compound is used, noodle rates (measured coming out of refiner following chill roll) are significantly lower in all cases than when silicone component(s) is used in the percentages claimed according to the subject invention. In addition, in all cases, except the 1% emulsion, the tackiness value is significantly lower when silicone component is used.

The reduced tackiness shows clearly that silicone is working as a processing aide and that the silicone can be used to increase noodle production in the first part of the process (thereby allowing overall total reduction rate to be more economically viable).

We claim:

1. A solid detergent bar composition consisting essentially of (percentages by weight):
   (a) from 10% to about 70% of a first synthetic surfactant which is an anionic surfactant;
   (b) from about 1% to about 20% of a second surfactant selected from the group consisting of second anionic surfactant different from the first, a nonionic surfactant, an amphoteric surfactant and mixtures thereof;
   (c) 0–35% free fatty acid:
   (d) 0–25% soap; and
   (e) consisting essentially of 0.1 to 0.5% of only one liquid silicone compound having a viscosity of 10,000 to 100,000 centistoke or an emulsion of only one liquid silicone compound and water having a viscosity of 10,000 to 100,000 centistoke.

2. A composition according to claim 1, wherein the first anionic surfactant is a $C_8$–$C_{18}$ acyl isethionate.

3. A composition according to claim 1, wherein the second surfactant is a betaine compound.

4. A composition according to claim 1, wherein the second surfactant is a sulfosuccinate compound.

5. A composition according to claim 1, wherein the second surfactant comprises a mixture of a betaine compound and a sulfosuccinate compound.

6. A composition according to claim 1, wherein the second surfactant is an alkoxylated isethionate.

7. A process for reducing tackiness and increasing noodle rate of soap noodles passing from a refiner to a silo for storing said noodles prior to subsequent processing which process comprises mixing:
   (a) from about 10% to about 70% of a first synthetic surfactant;
   (b) from about 1% to about 20% of a second surfactant selected from the group consisting of second anionic surfactant different than the first, a nonionic surfactant and amphoteric surfactant and mixtures thereof;
   (c) 0–35% free fatty acid;
   (d) 0–25% soap; and
   (e) 0.1 to 0.9% of a single silicone compound or mixture of liquid silicone compounds having a viscosity of from about 10,000 to about 200,000 centistokes.

* * * * *